US012714310B2

(12) United States Patent
Van Ee et al.

(10) Patent No.: US 12,714,310 B2
(45) Date of Patent: Aug. 25, 2026

(54) SYSTEM FOR PROVIDING STIMULATION

(71) Applicant: KONINKLIJKE PHILIPS N.V., Eindhoven (NL)

(72) Inventors: Raymond Van Ee, Geldrop (NL); Maria Estrella Mena Benito, Eindhoven (NL); Joanne Henriette Desiree Monique Westerink, Eindhoven (NL); Marieke van Dooren, Arendonk (BE); Timmy Robertus Maria Leufkens, Upplands Vasby (SE); Willem Huijbers, Tilburg (NL); Adrianus Johannes Maria Denissen, Moergestel (NL)

(73) Assignee: Koninklijke Philips N.V., Eindhoven (NL)

( * ) Notice: Subject to any disclaimer, the term of this patent is extended or adjusted under 35 U.S.C. 154(b) by 36 days.

(21) Appl. No.: 18/568,299

(22) PCT Filed: Jun. 9, 2022

(86) PCT No.: PCT/EP2022/065615

§ 371 (c)(1),
(2) Date: Dec. 8, 2023

(87) PCT Pub. No.: WO2022/258724

PCT Pub. Date: Dec. 15, 2022

(65) Prior Publication Data

US 2024/0277228 A1 Aug. 22, 2024

(30) Foreign Application Priority Data

Jun. 10, 2021 (EP) ..................................... 21178774

(51) Int. Cl.
*A61B 5/00* (2006.01)

(52) U.S. Cl.
CPC .......... *A61B 5/0036* (2018.08); *A61B 5/0042* (2013.01); *A61B 5/4848* (2013.01);
(Continued)

(58) Field of Classification Search
CPC ... A61B 5/0036; A61B 5/0042; A61B 5/4848; A61B 5/741; A61B 5/742; A61B 5/7455;
(Continued)

(56) References Cited

U.S. PATENT DOCUMENTS

| | | | | |
|---|---|---|---|---|
| 2001/0056231 A1* | 12/2001 | Jesmanowicz ......... | A61B 5/055 600/410 |
| 2002/0082495 A1* | 6/2002 | Biswal .............. | G01R 33/4806 324/307 |

(Continued)

FOREIGN PATENT DOCUMENTS

| | | | |
|---|---|---|---|
| CN | 106901739 | A | 6/2017 |
| EP | 2674193 | A1 | 12/2013 |
| WO | 2018165473 | A1 | 9/2018 |

OTHER PUBLICATIONS

Rachel Marsh et al., “A Virtual Reality Based FMRI Study of Reward Based Spatial Learning” Neuropsychologia 48(10) p. 2912-2921 Aug. 2010.

(Continued)

*Primary Examiner* — Baisakhi Roy

(57) ABSTRACT

A system and method for controlling rhythmic sensory stimulation provided to a subject with post-stroke depression, PSD, during an MRI scan. A control unit is configured to control a rhythmic sensory stimulation signal such that the signal is rhythmically synchronous to a scanning rhythm of an MRI scanner performing the MRI scan.

16 Claims, 3 Drawing Sheets

(52) U.S. Cl.
CPC .............. *A61B 5/741* (2013.01); *A61B 5/742* (2013.01); *A61B 5/7455* (2013.01)

(58) Field of Classification Search
CPC .... A61B 2505/09; A61B 5/055; A61B 5/4836
See application file for complete search history.

(56) References Cited

U.S. PATENT DOCUMENTS

| | | | | |
|---|---|---|---|---|
| 2005/0070787 | A1 | 3/2005 | Zeijlemaker | |
| 2007/0179558 | A1* | 8/2007 | Gliner | A61N 1/36082 607/45 |
| 2009/0018432 | A1 | 1/2009 | He et al. | |
| 2011/0257509 | A1* | 10/2011 | Olsen | A61B 5/055 600/411 |
| 2012/0056620 | A1* | 3/2012 | Feinberg | G01R 33/4835 324/309 |
| 2014/0180060 | A1 | 6/2014 | Parrish et al. | |
| 2016/0144167 | A1 | 5/2016 | Bakker et al. | |
| 2016/0259022 | A1* | 9/2016 | Beck | G01R 33/50 |
| 2018/0136299 | A1* | 5/2018 | Saint-Jalmes | G01R 33/58 |
| 2018/0333068 | A1* | 11/2018 | Beck | A61B 5/055 |
| 2018/0336680 | A1* | 11/2018 | Beck | A61B 5/0042 |
| 2018/0353761 | A1* | 12/2018 | Hochmair | A61B 5/12 |
| 2019/0159715 | A1 | 5/2019 | Mishra Ramanathan et al. | |
| 2020/0170534 | A1 | 6/2020 | Flaeschner et al. | |
| 2021/0393991 | A1* | 12/2021 | Miskovic | A61N 7/00 |
| 2022/0386949 | A1* | 12/2022 | Weiss | A61B 5/055 |
| 2023/0022546 | A1* | 1/2023 | Malchano | A61B 5/4064 |

OTHER PUBLICATIONS

International Search Report from PCT/EP2022/065615 mailed Jul. 13, 2022.

Bergmann & Frisén (2013). Why adults need new brain cells. Science 340 2013.

Cramer (2018). Treatments to Promote Neural Repair after Stroke. Journal of Stroke, 20, 57-70.

Degerman, et al. (2007) Human brain activity associated with audiovisual perception and attention. Neuroimage, 34, 1683-1691.

Feng et al. (2014). The neurobiological pathogenesis of poststroke depression. Scientific World Journal, 521349.

Jiang et al. (2015). Multisensory training reverses midbrain lesion-induced changes and ameliorates haemianopia. Nature Communications, 6.

Jones (2017). Motor compensation and its effects on neural reorganization after stroke. Nature Rev NeuroScience, 18.

Quaranta, et al (2008). Mood Disorders after Stroke: Diagnostic Validation of the Poststroke Depression Rating Scale. Cerebro Vasc Dis, 26: 237-243.

Towfighi et al. (2017). Poststroke Depression: A Scientific Statement for Healthcare Professionals. Stroke, 48, e30-e43.

van Ee, et al (2009) Multisensory congruency as a mechanism for attentional control over perceptual selection. J Neurosci, 29: 11641-11649.

Wahl et al. (2014). Asynchronous therapy restores motor control by rewiring of the rat corticospinal tract after stroke. Science, 344.

* cited by examiner

SYSTEM FOR PROVIDING STIMULATION

CROSS REFERENCE TO RELATED APPLICATIONS

This application is a U.S. national phase application of International Application No. PCT/EP2022/065615 filed on Jun. 9, 2022, which claims the benefit of EP Application Serial No. 21178774.2 filed on Jun. 10, 2021 and is incorporated herein by reference.

FIELD OF THE INVENTION

The invention relates to the field of providing stimulation to a subject, and in particular to providing stimulation to a subject with post-stroke depression.

BACKGROUND OF THE INVENTION

Post-stroke depression (PSD) is a common effect of a stroke, occurring in 30-50% of stroke survivors, and has a negative impact on the functional recovery, cognition and rehabilitation of stroke patients. In particular, PSD is associated with a higher risk of suboptimal recovery, recurrent vascular events, poor quality of life, and mortality.

Pharmacological (e.g. antidepressant medication) and psychotherapy (e.g. Cognitive Behavioral Therapy) approaches have both been used to treat PSD. While these approaches have proven to be beneficial for treating depression in general, they have limited efficacy in the case of PSD. This is, in part, due to problems caused by timing of intervention and/or side effects of medication, but also because these approaches do not take into account clinical and functional differences between patients, nor do they account for the physiological, rather than psychological, cause of PSD.

There is therefore a need for improved treatment for PSD.

SUMMARY OF THE INVENTION

The invention is defined by the claims.

According to examples in accordance with an aspect of the invention, there is provided a control unit for controlling stimulation provided to a subject with post-stroke depression during a magnetic resonance imaging, MRI, scan.

The control unit is configured to: control a rhythmic stimulation signal provided to the subject during the MRI scan, wherein the rhythmic stimulation signal is controlled to be synchronized with a scanning frequency of an MRI scanner performing the MRI scan.

The invention is based on the recognition that post-stroke depression, PSD, is physiological, rather than psychological, in origin, and may therefore be more effectively treated by repairing neuronal functions.

There is growing evidence to support the idea that functional neuronal repair may be beneficial in treating PSD. In particular, Feng et al. (2014), "The neurobiological pathogenesis of poststroke depression", Scientific World Journal, 521349 describes the beneficial effect of neurogenesis in repairing mood-related areas after stroke. The inventors propose that neurogenesis for perception-related brain areas may also be effective in treating PSD.

It is known that multisensory stimulation aids the brain in controlling attentional focus, particularly when applied rhythmically synchronously in at least two perceptual modalities (e.g., visual, auditory, tactile) simultaneously (see, for example, van Ee et al. (2009), "Multisensory congruency as a mechanism for attentional control over perceptual selection", Journal of Neuroscience, 29:11641-11649). Attentional focus is an important factor in engaging neurons in a particular task; the inventors therefore propose the use of attentional focus, controlled by the application of multisensory stimulation, to repair neural function.

A stimulation signal that is synchronized with the scanning frequency of the MRI signal provides (e.g. a change of) stimulations at a same or similar frequency (e.g. with peak amplitudes aligned or near-aligned) as the scanning frequency of the MRI. A rhythmic stimulation signal is one that provides a stimulation or a change of stimulation at predetermined time intervals (e.g. the beat of an audio signal). Since an MRI scanner automatically provides rhythmic sensory stimulation in the form of scanner noise, providing an additional rhythmic sensory stimulation signal during the MRI scan means that the subject is provided with rhythmic stimulation in two perceptual modalities simultaneously. In other words, the present disclosure proposes a mechanism by which at least two rhythmic stimulations are provided to the subject being scanned, including at least one rhythmic stimulation being a noise naturally generated by the MRI device.

A perceptual modality is a user-perceptible output, such that different forms of perceptual modalities provide different user-perceptible outputs. In some examples, the two perceptual modalities of the rhythmic stimulation may be the same (i.e., both are audio stimulation). For instance, the rhythmic stimulation signal may be music synchronized with the scanner's noise. In other examples, the rhythmic stimulation signal may provide stimulation in a different perceptual modality to the scanner noise. For instance, the rhythmic stimulation signal may be a visual or tactile signal. Any form of perceptual modality that can be rhythmically controlled is envisaged, including visual, audio and tactile outputs.

A rhythmic stimulation signal is any user-perceptible signal (e.g. a visual, audio or tactile signal) that has a controllable rhythm or "beat". Examples include music (which has a beat or rhythm), a moving image (which can move according to a beat or rhythm) and so on.

Providing the stimulation during an MRI scan allows the effect of the stimulation on affected brain regions and functional neuronal networks to be monitored. The stimulation may then be adjusted to improve the effectiveness of the stimulation.

The synchronization of the provided stimulation with the MRI scanning frequency ensures that interfering rhythms are not present while the stimulation is being provided, and means that the MRI images taken during the scan are all from the same section of the stimulation cycle, allowing a better comparison of brain activity between the images.

The stimulation may, for example, be provided to the subject during a resting state MRI scan or while the subject is engaged in a cognitive or perceptual task such as a memory task or visual detection task.

In some examples, the use of multisensory stimulation to treat PSD may be combined with pharmacological therapy and/or behavioral therapy. This may be more effective than any single approach used alone.

In some examples, the rhythmic stimulation signal is provided by the MRI scanner. This makes use of the fact that the MRI scanner may provide further sensory stimulation as a side effect of performing an MRI scan. For example, the MRI scanner may be used to provide a tactile stimulation signal, by intentionally inducing peripheral nerve stimulation (PNS) in the subject with a modulation according to the desired stimulation frequency. PNS occurs when the strong currents applied to the scanner's gradient coils excite sensorial and motor nerves in the subject, causing them to feel a tickling sensation or slight muscle contraction, and is generally considered an undesirable side effect of MRI scanning.

The rhythmic stimulation signal may be provided by a sensory stimulation system, e.g. a sensory stimulation system that is separate to the functionality of the MRI scanner.

The use of a separate sensory stimulation enables a greater flexibility in the type of stimulation offered to the patient, for example, visual stimulation, allowing the provision of more engaging stimulation than the MRI scanner is capable of providing.

The control unit may be further configured to: receive, from the MRI scanner, a sequence of images representative of brain activity of the subject taken during the MRI scan; and analyze an effect of the rhythmic stimulation signal based on the received sequence of images. This allows the stimulation to be adjusted in cases where the stimulation does not achieve a desired effect.

The control unit may be further configured to: determine an effectiveness of the rhythmic stimulation signal based on the analysis of the effect; and adjust the rhythmic stimulation signal in response to a determination that the effectiveness is below a predefined threshold. The stimulation signal may be adjusted, for example, by changing a type of stimulation, or by adjusting the stimulation rhythm.

The control unit may be further configured to control the scanning frequency of the MRI scanner. In this way, the control unit may adjust the frequency of the stimulation signal (for example, in order to improve an effectiveness of the provided stimulation) while keeping the stimulation signal and the MRI scanning frequency synchronized.

The rhythmic stimulation signal may be based on a personal preference of the subject. For example, the stimulation may be designed to take into account particular features or information that the subject finds engaging, such as images and/or recordings of the subject's family members/loved ones or images of preferred nature scenes.

In some examples, the control unit is further configured to provide the subject with reward-based interaction. In this way, dopamine release may be induced in the subject, further contributing towards neuronal repair.

There is also proposed a system for providing stimulation to a subject with post-stroke depression during an MRI scan, the system comprising: the control unit as herein described; and an MRI scanner, in communication with the control unit and configured to obtain a sequence of images representative of brain activity of the subject.

In some examples, the MRI scanner is further configured to provide the rhythmic stimulation signal based on an instruction from the control unit.

The system may further comprise a sensory stimulation system configured to provide the rhythmic stimulation signal based on an instruction from the control unit.

There is also proposed a computer-implemented method for controlling stimulation provided to a subject with post-stroke depression during an MRI scan. The computer-implemented method comprises: controlling a rhythmic stimulation signal provided to the subject during the MRI scan, wherein the rhythmic stimulation signal is controlled to be synchronized with a scanning frequency of an MRI scanner performing the MRI scan.

The computer-implemented method may further comprise receiving, from the MRI scanner, a sequence of images representative of brain activity of the subject taken during the MRI scan; and analyzing an effect of the rhythmic stimulation signal based on the received sequence of images.

The computer-implemented method may further comprise steps of: determining an effectiveness of the rhythmic stimulation signal based on the analysis of the effect; and adjusting the rhythmic stimulation signal in response to a determination that the effectiveness is below a predefined threshold.

There is also proposed a computer program product comprising computer program code means which, when executed on a computer device having a processing system, cause the processing system to perform all of the steps of the method. There is also proposed a (non-transitory) computer readable medium comprising the computer program product.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
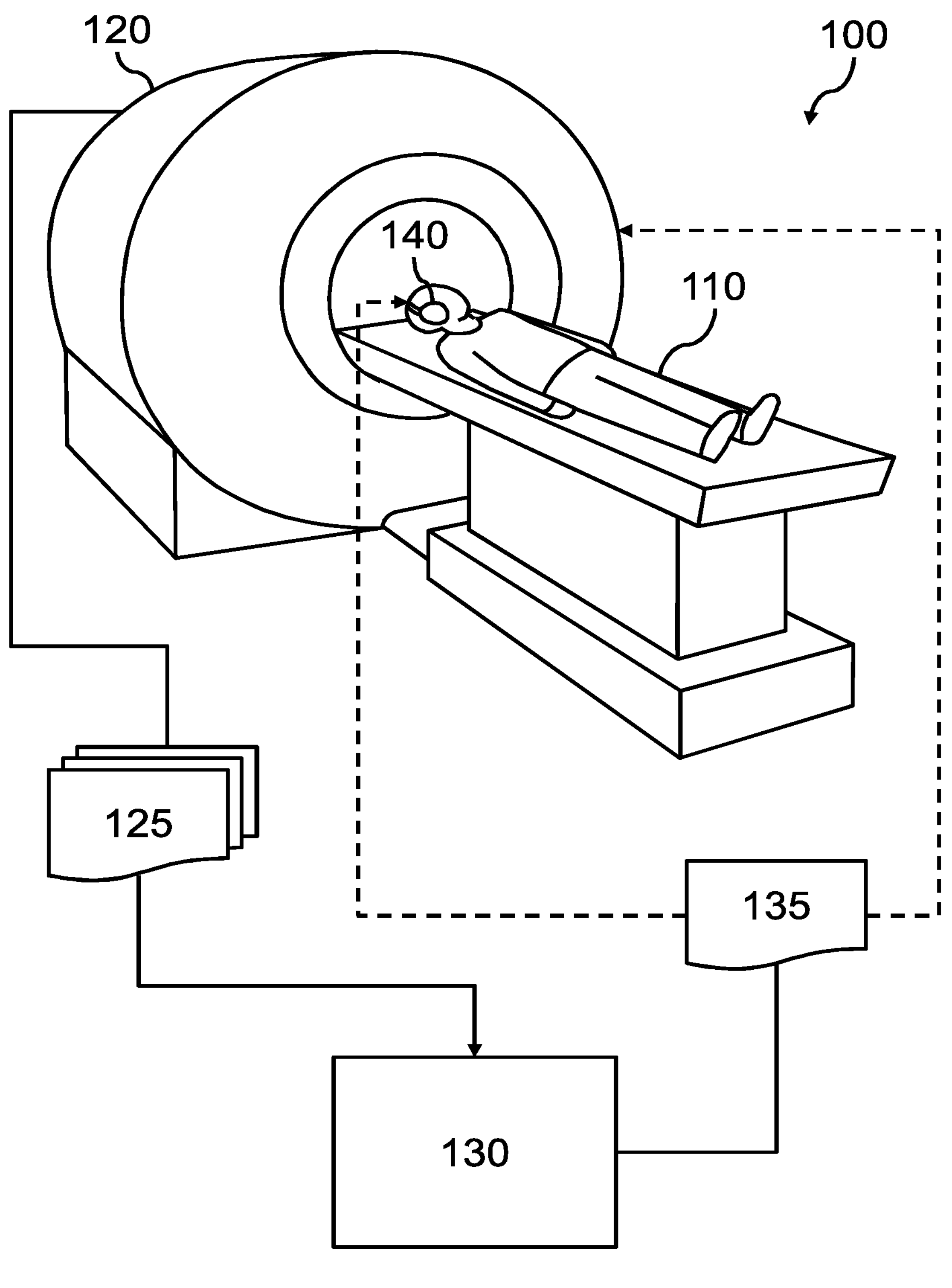
FIG. 1 illustrates a system according to an embodiment of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

According to a concept of the invention, there is proposed a system and method for controlling rhythmic sensory stimulation provided to a subject with post-stroke depression, PSD, during an MRI scan. A control unit is configured to control a rhythmic sensory stimulation signal such that the signal is rhythmically synchronous to a scanning rhythm of an MRI scanner performing the MRI scan.

Embodiments are at least partly based on the realizations that multisensory stimulation is effective in improving attentional focus, that attentional focus may play an important role in repairing neuronal function, and that functional neuronal repair may be effective in treating PSD.

The inventors propose that, since failure of neuronal functions is at least partly responsible for the occurrence of PSD in a subject, PSD may be treated by repairing the relevant neuronal functions. Repairing neuronal function is considered distinct from repairing a particular damaged "brain area": for example, a cognitive function such as memory may be repaired (e.g. by performing exercises) without necessarily repairing the damaged memory neurons. The inventors propose that the use of attentional focus may aid the repair of neuronal function, since attentional focus is an important factor in engaging neurons in a particular task.

Research has shown that immersive multisensory stimulation aids the brain in controlling attentional focus, particularly when the stimulation is applied rhythmically synchronously in at least two perceptual modalities simultaneously, as heteromodal congruency allows the brain to identify signal relevance in a bombardment of sensory signals.

The inventors have recognized that an MRI scanner produces a rhythmic noise while performing a scan, and that this may be considered a first form of rhythmic sensory stimulation of a rhythmic multisensory stimulation provided to the subject if the subject is also provided with a second form of rhythmic sensory stimulation synchronized to the scanner noise. In other words, the invention makes use of the noise produced by the scanner during an MRI scan by combining the noise with a rhythmic sensory stimulation signal synchronized to the scanning rhythm to provide an immersive multisensory stimulation therapy for treating PSD.

Illustrative embodiments may, for example, be employed in MRI scanning systems.

FIG. 1 illustrates a system 100 for providing rhythmic multisensory stimulation to a subject 110 with post-stroke depression during an MRI scan, according to an embodiment of the invention. The system comprises an MRI scanner 120 and a control unit 130. The control unit is, itself, an embodiment of the invention. In some embodiments, the system further comprises a sensory stimulation system 140.

The MRI scanner 120 performs an MRI scan on the subject 110 to obtain a sequence of images 125 representative of brain activity of the subject. As the MRI scanner performs the scan, the scanner automatically produces a rhythmic noise, with the rhythm dependent on the scanning parameters of the MRI scan. This noise is caused by vibrations of the gradient coils in the MRI scanner.

The control unit 130 is configured to control rhythmic sensory stimulation provided to the subject 110 (e.g. via the sensory stimulation system 140), by controlling a (first) rhythmic stimulation signal 135 such that the signal is synchronized with a scanning frequency of the MRI scanner 120 and, therefore, with the rhythmic noise produced by the MRI scanner 120. In this way, the subject is provided with two types of rhythmic and synchronous stimulation simultaneously: the rhythmic noise of the scanner, and the rhythmic stimulation signal controlled by the control unit.

The rhythmic stimulation signal 135 may be independent of the effectiveness and/or operation of the MRI scan itself. In particular, the rhythmic stimulation signal may control a stimulation that does not result from a conventional or intended operation of a conventional MRI scan.

The rhythmic stimulation signal 135 may be provided in any suitable perceptual modality. For example, the rhythmic stimulation signal may be an audio signal, in which case the subject 110 is provided with two types of audio stimulation (the scanner noise and the audio stimulation via the rhythmic stimulation signal). The rhythmic stimulation signal may therefore control, for example, the operation of a speaker or speakers (e.g. in headphones or a headset).

It is recognized that the effectiveness of the stimulation in improving attentional focus in the subject may be improved by providing the rhythmic stimulation signal to provide a stimulation in a different perceptual modality to the scanner noise (i.e. a perceptual modality other than audio). For example, the rhythmic stimulation signal may be a signal that controls a visual or tactile output (e.g. to provide visual or tactile stimulation).

In some examples, the control unit 130 may control a plurality of different rhythmic stimulation signals provided to the subject 110, each controlled to provide a rhythmic stimulation that is synchronized with the scanning frequency of an MRI scanner. Provision of multiple rhythmic stimulation is considered to increase an effectiveness of cognitive function repair. The plurality of rhythmic stimulation signals may have different perceptual modalities. This approach will increase the likelihood of success.

In some examples, the control unit 130 may obtain the scanning frequency of the MRI scanner 120 from the MRI scanner or based on an input from an operator of the MRI scanner, and determine a desired rhythm of the rhythmic stimulation signal based on the obtained scanning frequency. In other examples, the control unit may control the scanning frequency of the MRI scanner as well as the rhythmic stimulation signal, e.g. the control unit may form part of a control system for the MRI scanner.

In some examples, both kinds of rhythmic sensory stimulation are provided by the MRI scanner 120. In other words, the MRI scanner may provide the (rhythmic simulation provided by the) rhythmic stimulation signal in addition to producing the rhythmic scanner noise. For instance, the MRI scanner may provide a rhythmic tactile stimulation signal in the form of peripheral nerve stimulation (PNS). PNS is a side-effect of MRI scanning that occurs when the strong currents applied to the gradient coils of the MRI scanner excite sensorial and motor nerves in the subject. The subject typically feels this as a ticking sensation or spontaneous slight muscle contraction at their arms or back. This effect occurs particularly in newer MRI scanners with higher magnetic strengths, such as 7 tesla scanners.

PNS is generally considered an undesirable side-effect, and the scanning parameters of the MRI scan are set to avoid or reduce PNS. Here, the control unit 130 may cause PNS to be intentionally induced in the subject 110 by providing an additional modulation of the gradient coil signals with a desired periodicity.

In other examples, such as the system 100 shown in FIG. 1, the rhythmic stimulation signal is provided by a sensory stimulation system 140, which receives instructions from the control unit 130 and is separate and/or distinct to the MRI scanner (i.e. does not contribute to the generation of MRI images).

In FIG. 1, the sensory stimulation system comprises a pair of headphones for providing an audio signal (e.g. music), but the sensory stimulation system may comprise any device(s) suitable for providing rhythmic sensory stimulation in one or more perceptual modalities (e.g. audio, visual and/or tactile). In some examples, the sensory stimulation system may be configured to provide a variety of different stimulation signals to a subject. This allows the provision of multiple rhythmic sensory stimulation signals simultaneously and allows a type of stimulation to be changed if a particular stimulation signal does not produce a desired effect in the subject.

For example, the sensory stimulation system may comprise a wearable device that may be worn by the subject 110 during the MRI scan, such as headphones, a virtual reality headset and/or a wearable patch for providing haptic feedback, or a device fitted to the MRI scanner 120, such as a speaker within the scanner bore, a display unit disposed on the inside of the scanner bore, and/or a light emitting device within the scanner bore. Further examples of suitable means for providing rhythmic sensory stimulation to a subject during an MRI scan will be apparent to the skilled person.

An example of a suitable audio stimulation is music, speech (e.g. poetry) or other rhythmic sounds. An example of a suitable visual stimulation comprises images (e.g. a slideshow of images) or a rhythmic visualization (e.g. a pulsating or moving image or rendering). An example of a suitable tactile stimulation includes a vibration (e.g. of a vibration element in contact with the subject) or a massaging effect. Other suitable examples will be readily apparent to the skilled person.

The sequence of images 125 obtained by the MRI scanner 120 during the scan may be used to analyze and evaluate an efficacy of the rhythmic sensory stimulation on the subject, and the rhythmic sensory stimulation may be adjusted as required depending on the efficacy. For example, by employing real-time fMRI, brain activity in brain regions and/or functional neuronal networks affected by the stroke may be monitored as the stimulation is provided to the subject 110.

The subject may simply lie still in the scanner bore during the MRI scan (i.e., the MRI scan may be a resting state MRI scan). Alternatively, the subject may be engaged in one or more cognitive or perceptual tasks during the MRI scan. This may allow the effect of the stimulation to be more accurately determined by tailoring the task to the affected brain regions and/or functional neuronal networks. For example, a subject who has suffered a stroke that has affected brain regions associated with memory may be asked to perform a memory task during the MRI scan, while a subject who has suffered a stroke that has affected brain regions associated with visual perception may be given a visual detection task.

The effect of the stimulation may be determined by a medical specialist, e.g. an operator of the MRI scan, based on a display of the obtained sequence of images 125, and the stimulation provided to the subject may be adjusted based on an input from the medical specialist.

Alternatively, the control unit 130 may be configured to receive the sequence of images 125 from the MRI scanner 120 and analyze an effect of the stimulation based on the received sequence of images. The control unit may analyze the effect of the stimulation by, for example, comparing one or more images obtained before the stimulation was provided to the subject with one or more images obtained while the stimulation was being applied, in order to determine a change in the subject's brain activity. Computer-implemented methods for analyzing MRI images are well known, and any suitable method for detecting a change in brain activity may be used by the control unit. In some examples, the control unit may analyze the effect based on whether a change in brain activity is determined in one or more particular brain regions and/or functional neuronal networks.

The control unit 130 may be configured to provide an indication of the effect of the stimulation to an operator of the MRI scan, for example, via a display unit (not shown), to allow the operator to determine whether an adjustment to the stimulation is required. Alternatively, the control unit may be configured to determine whether an adjustment to the stimulation is required and to adjust the stimulation accordingly.

For example, the control unit 130 may be configured to determine an effectiveness of the rhythmic stimulation provided to the subject 110 based on the analysis of the effect of the stimulation. An effectiveness may, for instance, comprise a measure or indicator of effectiveness or success of providing the rhythmic stimulation to the subject. In some examples, an effectiveness may be generated by comparing MRI image data obtained before the rhythmic stimulation signal to MRI image data obtained whilst the rhythmic stimulation signal is provided to the subject.

An effectiveness may, for example, comprise a measure of a difference between brain activity (e.g. in a predetermined portion of the brain) before the rhythmic stimulation signal is provided and while the rhythmic stimulation signal is being provided. Brain activity is measurable and identifiable from MRI data, e.g. from functional MRI data (fMRI data). For example, the effectiveness may comprise a percentage change in the number of active voxels in the fMRI data.

Methods for measuring a change in brain activity based on fMRI data, and in particular measuring a brain response to stimuli, are well known. See, for example, Lindquist (2008), "The statistical analysis of fMRI data", Statistical Science 23(4):439-464, and Martuzzi et al. (2007), "Multisensory interactions within human primary cortices revealed by BOLD dynamics", Cerebral Cortex, 17(7):1672-1679.

In some examples, the effectiveness may comprise a measure of attentional focus. For instance, the effectiveness may comprise a measure of a difference in brain activity before the rhythmic stimulation signal is provided and while the rhythmic stimulation signal is being provided in brain regions and/or neuronal networks associated with attentional focus.

The effect of attentional focus on brain activity, and the brain regions and networks in which the effect is observed are well known: see, for example, Degerman et al. (2007), "Human brain activity associated with audiovisual perception and attention", Neuroimage, 34:1683-1691, Saenz et al. (2002), "Global effects of feature-based attention in human visual cortex", Nature Neuroscience, 5(7):631-632, Schwartz et al. (2004), "Attentional load and sensory competition in human vision: modulation of fMRI responses by load at fixation during task-irrelevant stimulation in the peripheral visual field", Cerebral Cortex, 15(6):770-786, Milham et al. (2002), "Attentional control in the aging brain: insights from an fMRI study of the Stroop task", Brain and Cognition, 49(3):277-296, and Raisbeck et al. (2020), "The effects of attentional focus on brain function during a gross motor task", Journal of Sport Rehabilitation, 29(4):441-447.

The control unit may determine that an adjustment to the stimulation is required if the effectiveness is determined to be below a predefined threshold. In other words, the control unit may adjust the rhythmic stimulation signal based on a determination that the effectiveness of the rhythmic stimulation is below the threshold.

An adjustment to the stimulation may comprise a change in the type of stimulation provided (e.g. a change in perceptual modality) and/or a change in the rhythm of the stimulation. If the rhythm of the stimulation is adjusted, the scanning frequency of the MRI scan may also be adjusted so that the rhythmic stimulation remains synchronized with the scanner noise. This may be achieved by instructing an operator of the MRI scanner 120 to adjust the scanning parameters, or by configuring the control unit 130 to control the scanning frequency of the MRI scanner.

In this way, the system 100 may effectively operate as a closed loop (feedback) system configured to tailor the rhythmic stimulation to the subject 110, by monitoring the effect of the rhythmic stimulation as the rhythmic stimulation is adjusted, until a desired effect of the rhythmic stimulation is detected in the brain activity of the subject.

For example, a subject whose visual perception has been affected by a stroke may complete a visual detection task during the MRI scan. The control unit 130 may then determine, based on MRI images obtained during the scan, whether the rhythmic stimulation provided to the subject produces a desired increase in brain activity in the functional neuronal networks involved in the successful detection of a visual object in a particular part of the visual field. If the desired increase is not observed, the control unit may adjust the rhythmic stimulation signal, and optionally the scanning frequency of the MRI scanner, until the desired increase is detected in the subject's brain activity.

In some examples, the rhythmic stimulation signal may be based on a personal preference of the subject 110. For instance, the subject may be provided with images/pictures and/or voices of family members/loved ones or with images/pictures of preferred nature scenes. Where the stimulation comprises images, a change or transition between different images (e.g. the frequency of changing an image) may be rhythmically synchronous with the MRI scanning frequency. This may improve the subject's engagement with the rhythmic stimulation signal, improving its efficacy.

In some examples, gamification techniques may be used to provide the subject 110 with additional pleasure while the rhythmic stimulation is applied, leading to dopaminergic facilitation of neuronal repair. For instance, the control unit 130 may be configured to provide reward-based interaction in addition to, or as part of, the rhythmic stimulation. The reward-based interaction may be provided by the sensory stimulation system 140, e.g. by providing user-preferred stimulation, or by a separate interactive system. In some examples, the sensory stimulation system may include a user-input device.

The reward-based interaction may be tailored to the subject 110. For example, a subject who has difficulty in moving their left arm following a stroke may be presented with targets that the subject should point at with their left arm, and rewarded with points when they succeed in pointing at the target. The interaction may further be designed to increase in difficulty as the subject's performance improves.

In some examples, the system 100 may be used in combination with existing therapies for PSD (i.e. pharmacological and/or psychotherapy treatments) to improve an effectiveness of the treatment. The inventors have recognized that, in some cases, PSD may be caused by a complex combination of many factors in addition to the failure of neuronal function. This may particularly be the case when the depression has existed for a prolonged period of time.

Figure 2:
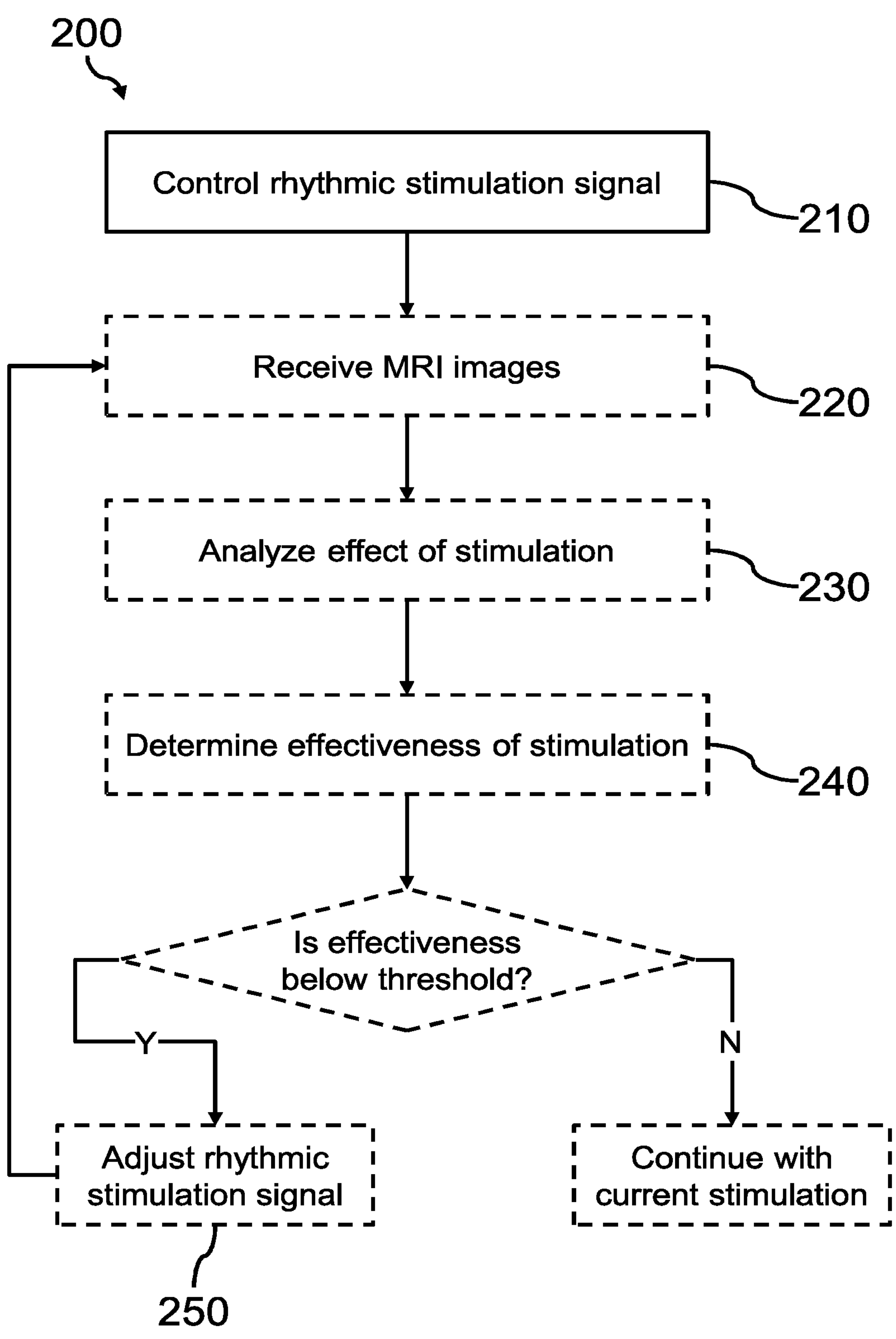
FIG. 2 is a flowchart illustrating a computer-implemented method according to an embodiment.

FIG. 2 illustrates a computer-implemented method 200 for controlling multisensory stimulation provided to a subject with post-stroke depression during an MRI scan, according to an embodiment of the invention.

The method comprises step 210, in which a rhythmic stimulation signal provided to the subject is controlled such that the rhythmic stimulation signal is synchronized with a scanning frequency of an MRI scanner performing the MRI scan.

In some examples, the method further comprises steps 220 and 230. At step 220, a sequence of images representative of brain activity of the subject taken during the MRI scan is received from the MRI scanner. At step 230, an effect of the rhythmic stimulation on the subject is analyzed based on the received sequence of images.

In some examples, the method further comprises step 240, in which an effectiveness of the rhythmic stimulation is determined based on the analysis of the effect. If the effectiveness is found to be below a predefined threshold, the method may proceed to step 250, in which the rhythmic stimulation signal is adjusted. Otherwise, a current rhythmic stimulation signal may continue to be provided to the subject.

In some examples, steps 220 to 250 may be repeated until it is determined that a current rhythmic stimulation signal has a desired effect (i.e. the effectiveness is no longer below the predefined threshold).

Figure 3:
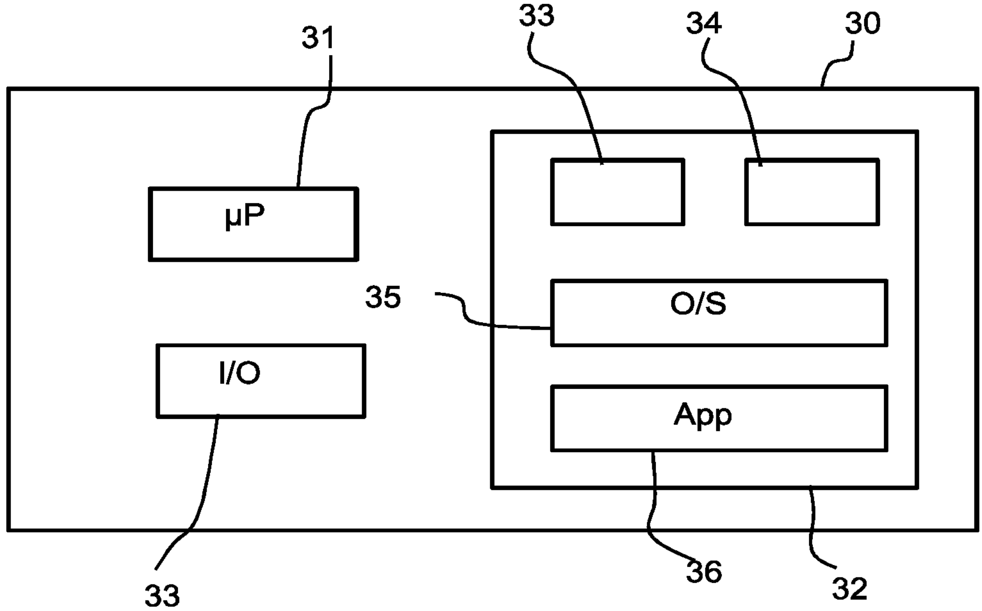
FIG. 3 illustrates a control unit according to an embodiment.

By way of further example, FIG. 3 illustrates an example of a control unit 30 (e.g. a computer) within which one or more parts of an embodiment may be employed. Various operations discussed above may utilize the capabilities of the control unit 30. For example, one or more parts of a system for controlling stimulation to a subject may be incorporated in any element, module, application, and/or component discussed herein. In this regard, it is to be understood that system functional blocks can run on a single control unit or may be distributed over several control units and locations (e.g. connected via internet).

The control unit 30 includes, but is not limited to, PCs, workstations, laptops, PDAs, palm devices, servers, storages, and the like. Generally, in terms of hardware architecture, the control unit may include one or more processors 31, memory 32, and one or more I/O devices 37 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 31 is a hardware device for executing software that can be stored in the memory 32. The processor 31 can be virtually any custom made or commercially available processor, a central processing unit (CPU), a digital signal processor (DSP), or an auxiliary processor among several processors associated with the control unit 30, and the processor 31 may be a semiconductor based microprocessor (in the form of a microchip) or a microprocessor.

The memory 32 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 32 may incorporate electronic, magnetic, optical, and/or other types of storage media. Note that the memory 32 can have a distributed architecture, where various components are situated remote from one another, but can be accessed by the processor 31.

The software in the memory 32 may include one or more separate programs, each of which comprises an ordered listing of executable instructions for implementing logical functions. The software in the memory 32 includes a suitable operating system (O/S) 35, compiler 34, source code 33, and one or more applications 36 in accordance with exemplary embodiments. As illustrated, the application 36 comprises numerous functional components for implementing the features and operations of the exemplary embodiments. The application 36 of the control unit 30 may represent various applications, computational units, logic, functional units, processes, operations, virtual entities, and/or modules in accordance with exemplary embodiments, but the application 36 is not meant to be a limitation.

The operating system 35 controls the execution of other computer programs, and provides scheduling, input-output control, file and data management, memory management, and communication control and related services. It is contemplated by the inventors that the application 36 for implementing exemplary embodiments may be applicable on all commercially available operating systems.

Application 36 may be a source program, executable program (object code), script, or any other entity comprising a set of instructions to be performed. When a source program, then the program is usually translated via a compiler (such as the compiler 34), assembler, interpreter, or the like, which may or may not be included within the memory 32, so as to operate properly in connection with the O/S 35. Furthermore, the application 36 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 37 may include input devices such as, for example but not limited to, a mouse, keyboard, scanner, microphone, camera, etc. Furthermore, the I/O devices 37 may also include output devices, for example but not limited to a printer, display, etc. Finally, the I/O devices 37 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 37 also include components for communicating over various networks, such as the Internet or intranet.

If the control unit 30 is a PC, workstation, intelligent device or the like, the software in the memory 32 may further include a basic input output system (BIOS) (omitted for simplicity). The BIOS is a set of essential software routines that initialize and test hardware at startup, start the O/S 35, and support the transfer of data among the hardware devices. The BIOS is stored in some type of read-only-memory, such as ROM, PROM, EPROM, EEPROM or the like, so that the BIOS can be executed when the control unit 30 is activated.

When the control unit 30 is in operation, the processor 31 is configured to execute software stored within the memory 32, to communicate data to and from the memory 32, and to generally control operations of the control unit 30 pursuant to the software. The application 36 and the O/S 35 are read, in whole or in part, by the processor 31, perhaps buffered within the processor 31, and then executed.

When the application 36 is implemented in software it should be noted that the application 36 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 36 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

It will be understood that the disclosed methods are computer-implemented methods. As such, there is also proposed a concept of a computer program comprising code means for implementing any described method when said program is run on a processing system.

As discussed above, embodiments make use of a control unit. The control unit can be implemented in numerous ways, with software and/or hardware, to perform the various functions required. A processor is one example of a control unit which employs one or more microprocessors that may be programmed using software (e.g. microcode) to perform the required functions. A control unit may however be implemented with or without employing a processor, and also may be implemented as a combination of dedicated hardware to perform some of the functions and a processor (e.g. one or more programmed microprocessors and associated circuitry) to perform other functions.

Examples of control unit components that may be employed in various embodiments of the present disclosure include, but are not limited to, conventional microprocessors, application specific integrated circuits (ASICs), and field-programmable gate arrays (FPGAs).

In various implementations, a processor or control unit may be associated with one or more storage media such as volatile and non-volatile control unit memory such as RAM, PROM, EPROM, and EEPROM. The storage media may be encoded with one or more programs that, when executed on one or more processors and/or control units, perform the required functions. Various storage media may be fixed within a processor or control unit or may be transportable, such that the one or more programs stored thereon can be loaded into a processor or control unit.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted that the term "adapted to" is intended to be equivalent to the term "configured to". Any reference signs in the claims should not be construed as limiting the scope.

The invention claimed is:

1. A system comprising:

a magnetic resonance imaging (MRI) scanner configured to obtain a sequence of images representative of brain activity of a subject during an MRI scan, wherein the MRI scanner provides a first rhythmic stimulation signal representative of noise of the MRI scanner;

a sensory stimulation system configured to provide a second rhythmic stimulation signal to the subject during the MRI scan, wherein the second rhythmic stimulation signal is a user-perceptible signal including at least one of a visual signal, an audio signal, or a tactile signal; and a control unit configured to control the second rhythmic stimulation signal provided to the subject during the MRI scan, wherein the second rhythmic stimulation signal is controlled to be synchronized with a scanning frequency of the MRI scanner performing the MRI scan and the first rhythmic stimulation signal representative of noise of the MRI scanner, and wherein the first rhythmic stimulation signal and the second rhythmic stimulation signal provide an immersive multisensory stimulation therapy.

2. The system of claim 1, wherein the control unit is further configured to:

analyze an effect of the second rhythmic stimulation signal based on the sequence of images.

3. The system of claim 2, wherein the control unit is further configured to:

determine an effectiveness of the second rhythmic stimulation signal based on an analysis of the effect; and adjust the second rhythmic stimulation signal in response to a determination that the effectiveness is below a predefined threshold.

4. The system of claim 1, wherein the control unit is further configured to control the scanning frequency of the MRI scanner.

5. The system of claim 1, wherein the second rhythmic stimulation signal is based on a personal preference of the subject.

6. The system of claim 1, wherein the control unit is further configured to provide the subject with a reward-based interaction.

7. The system of claim 1, wherein the MRI scanner is further configured to provide the first rhythmic stimulation signal based on an instruction from the control unit.

8. The system of claim 1, further comprising presenting the rhythmic stimulation signal in a different user perceptual modality than a prior rhythmic stimulation signal last presented to a user.

9. A computer-implemented method for controlling stimulation provided to a subject with post-stroke depression during an MRI scan, the computer-implemented method comprising:

controlling a first rhythmic stimulation signal provided to the subject during the MRI scan, wherein the first rhythmic stimulation signal is a user-perceptible signal including at least one of a visual signal, an audio signal, or a tactile signal, and wherein the first rhythmic stimulation signal is controlled to be synchronized with a scanning frequency of an MRI scanner performing the MRI scan and with a second rhythmic stimulation signal, wherein noise associated with the MRI scanner provides the second rhythmic stimulation signal to the subject, and wherein the first rhythmic stimulation signal and the second rhythmic stimulation signal provide an immersive multisensory stimulation therapy for the post-stroke depression.

10. The computer-implemented method of claim 9, further comprising:

receiving, from the MRI scanner, a sequence of images representative of brain activity of the subject taken during the MRI scan; and analyzing an effect of the first rhythmic stimulation signal based on the sequence of images.

11. The computer-implemented method of claim 10, further comprising:

determining an effectiveness of the first rhythmic stimulation signal based on an analysis of the effect; and adjusting the first rhythmic stimulation signal in response to a determination that the effectiveness is below a predefined threshold.

12. The computer implemented method of claim 11, further comprising providing the rhythmic stimulation signal in a different user perceptual modality than a prior rhythmic stimulation signal last presented to a user.

13. A computer program product comprising computer program code stored on a non-transitory computer readable medium which, when executed on a computer device having a processing system, cause the processing system to perform the method according to claim 9.

14. A computer implemented method comprising:

receiving an input indicative of a rhythmic stimulation signal representative of noise produced by a magnetic resonance imaging (MRI) scanner during an MRI scan;

outputting a sensory stimulation signal to an associated subject undergoing the MRI scan, wherein the sensory stimulation signal is a user-perceptible signal including at least one of a visual signal, an audio signal, or a tactile signal;

controlling the output of the sensory stimulation signal to be synchronized with a scanning frequency of the MRI scanner and with the rhythmic stimulation signal representative of noise produced by the MRI scanner; and receiving a sequence of images representative of brain activity of the subject taken during the MRI scan; and analyzing an effect of the rhythmic stimulation on the subject based on the sequence of images, and wherein the rhythmic stimulation signal and the sensory stimulation signal provide an immersive multisensory stimulation therapy.

15. The computer implemented method of claim 14, further comprising adjusting a frequency of the rhythmic stimulation signal based on a determined effectiveness from the analyzing the effect of the rhythmic stimulation on the subject based on the sequence of images.

16. The computer implemented method of claim 14, further comprising providing the rhythmic stimulation signal in a different user perceptual modality than a prior rhythmic stimulation signal last presented to a user.

* * * * *